(12) United States Patent
Rao et al.

(10) Patent No.: US 9,388,373 B2
(45) Date of Patent: Jul. 12, 2016

(54) MICROSCALE BIOPROCESSING SYSTEM AND METHOD FOR PROTEIN MANUFACTURING

(75) Inventors: Govind Rao, Ellicott City, MD (US); Yordan Kostov, Columbia, MD (US); Leah Tolosa, Columbia, MD (US); Lam Hung, Baltimore, MD (US); Xudong Ge, Woodstock, MD (US); Douglas Frey, Ellicott City, MD (US); Virendra Singh, Baltimore, MD (US)

(73) Assignee: University of Maryland Baltimore County, Baltimore, MD (US)

( * ) Notice: Subject to any disclaimer, the term of this patent is extended or adjusted under 35 U.S.C. 154(b) by 97 days.

(21) Appl. No.: 13/823,911

(22) PCT Filed: Mar. 8, 2012

(86) PCT No.: PCT/US2012/028358
§ 371 (c)(1),
(2), (4) Date: Jun. 28, 2013

(87) PCT Pub. No.: WO2012/122413
PCT Pub. Date: Sep. 13, 2012

(65) Prior Publication Data
US 2013/0280797 A1 Oct. 24, 2013

Related U.S. Application Data

(60) Provisional application No. 61/450,191, filed on Mar. 8, 2011.

(51) Int. Cl.
*C12M 1/40* (2006.01)
*C12M 1/00* (2006.01)
*C12M 1/36* (2006.01)

(52) U.S. Cl.
CPC ............. *C12M 21/18* (2013.01); *C12M 21/14* (2013.01); *C12M 41/48* (2013.01); *C12M 43/00* (2013.01); *C12M 47/12* (2013.01)

(58) Field of Classification Search
CPC ...... C12M 47/12; C12M 21/18; C12M 43/00; C12M 41/48; C12M 21/14
See application file for complete search history.

(56) References Cited

U.S. PATENT DOCUMENTS

| | | | | |
|---|---|---|---|---|
| 6,670,173 B1 * | 12/2003 | Schels et al. | ........... | C12M 21/18 435/287.2 |
| 6,673,532 B2 * | 1/2004 | Rao | ................................. | 435/4 |
| 6,946,075 B2 * | 9/2005 | Kopf | .............................. | 210/635 |
| 9,163,272 B2 | 10/2015 | Park et al. | | |
| 2008/0287656 A1 * | 11/2008 | Peters et al. | .................. | 530/350 |

* cited by examiner

*Primary Examiner* — Gautam Prakash
(74) *Attorney, Agent, or Firm* — Rene A. Vazquez, Esq.

(57) ABSTRACT

A bioprocessing system for protein manufacturing is provided that is compact, integrated and suited for on-demand production and delivery of therapeutic proteins to patients. The system can also be used for efficient on-demand production of any type of protein.

19 Claims, 8 Drawing Sheets

US 9,388,373 B2

MICROSCALE BIOPROCESSING SYSTEM AND METHOD FOR PROTEIN MANUFACTURING

This application claims priority to U.S. Provisional Application Ser. No. 61/450,191, filed Mar. 8, 2011, whose entire disclosure is incorporated herein by reference.

BACKGROUND OF THE INVENTION

1. Field of the Invention

The present invention relates to protein manufacturing and, more particularly, to an integrated and compact bioprocessing system for the production or manufacturing of proteins.

2. Background of the Related Art

The time it takes for a new drug to reach the market is 8-10 years at a cost approaching $1.2 billion. Many of these new drug entities are referred to as biologics (e.g., a protein used as a drug or therapeutic). These are molecules produced by living cells in vitro using cell culture and fermentation technologies. Stringent process control is required since changes in culture conditions can lead to, for example, altered glycosylation profiles, which can then drastically change the drug's pharmacokinetics, efficacy and immunogenicity. Therefore, much effort towards FDA approval is devoted to the development of documented and robust manufacturing processes that will produce safe and efficacious biologics of consistent quality. These are collectively referred to as good manufacturing processes (GMP). The goal is to arrive at a process that is well defined and reproducible, and that leads to products that meet pre-determined characteristics of quality, identity, purity, safety and efficacy.

Biologics are currently produced in a centralized manufacturing facility with large scale (>10,000 liters) cell cultures, and with the necessary large volume separation, purification, formulation, packaging, and distribution infrastructure (e.g. a typical Merck, Pfizer or Genentech plant). The time period from a cell bank to the final delivery of the therapeutic vial is on the order of 6-8 weeks under ideal conditions and produces batches of around 10 Kg bulk protein. As shown in FIG. 1, the process itself is complex. FIG. 1 shows a typical flow sheet for the manufacturing of protein biologics—both for proteins that are expressed intracellularly and proteins expressed extracellularly. Every step needs to be individually developed, scaled-up, optimized and validated in a manufacturing setting. The final product will also have an expiration date and is either shipped lyophilized or via a cold chain, which must also be documented.

SUMMARY OF THE INVENTION

An object of the invention is to solve at least the above problems and/or disadvantages and to provide at least the advantages described hereinafter.

Therefore, an object of the present invention is to provide an integrated and compact bioprocessing system for the production of proteins.

Another object of the present invention is to provide an integrated and portable bioprocessing system for the production of proteins.

Another object of the present invention is to provide an integrated and compact bioprocessing system for protein expression and purification.

Another object of the present invention is to provide a method for on-demand production and delivery of a therapeutic protein to a patient.

To achieve at least the above objects, in whole or in part, there is provided a bioprocessing system comprising a production module for producing a protein and a purification module for receiving the protein from the production module and for purifying the protein from reagents.

To achieve at least the above objects, in whole or in part, there is also provided a bioprocessing system, comprising a reactor for protein expression, a membrane chromatography component for receiving and purifying protein output by the reactor and a diafiltration component for receiving purified protein from the membrane chromatography and for further purifying the purified protein.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

The present invention is particularly suited for the on-demand manufacturing of therapeutic proteins (either cell-based or cell-free) that are suitable for direct delivery to a patient. Therefore, the present invention will be primarily described and illustrated in connection with the manufacturing of therapeutic proteins. However, the present invention can also be used to manufacture any type of protein. Further, the present invention is particularly suited for the on-demand manufacturing of proteins using cell-free expression, and thus the present invention will be described primarily in the context of cell-free protein expression. However, the present invention can also be used in connection with cell-based protein expression.

Figure 1:
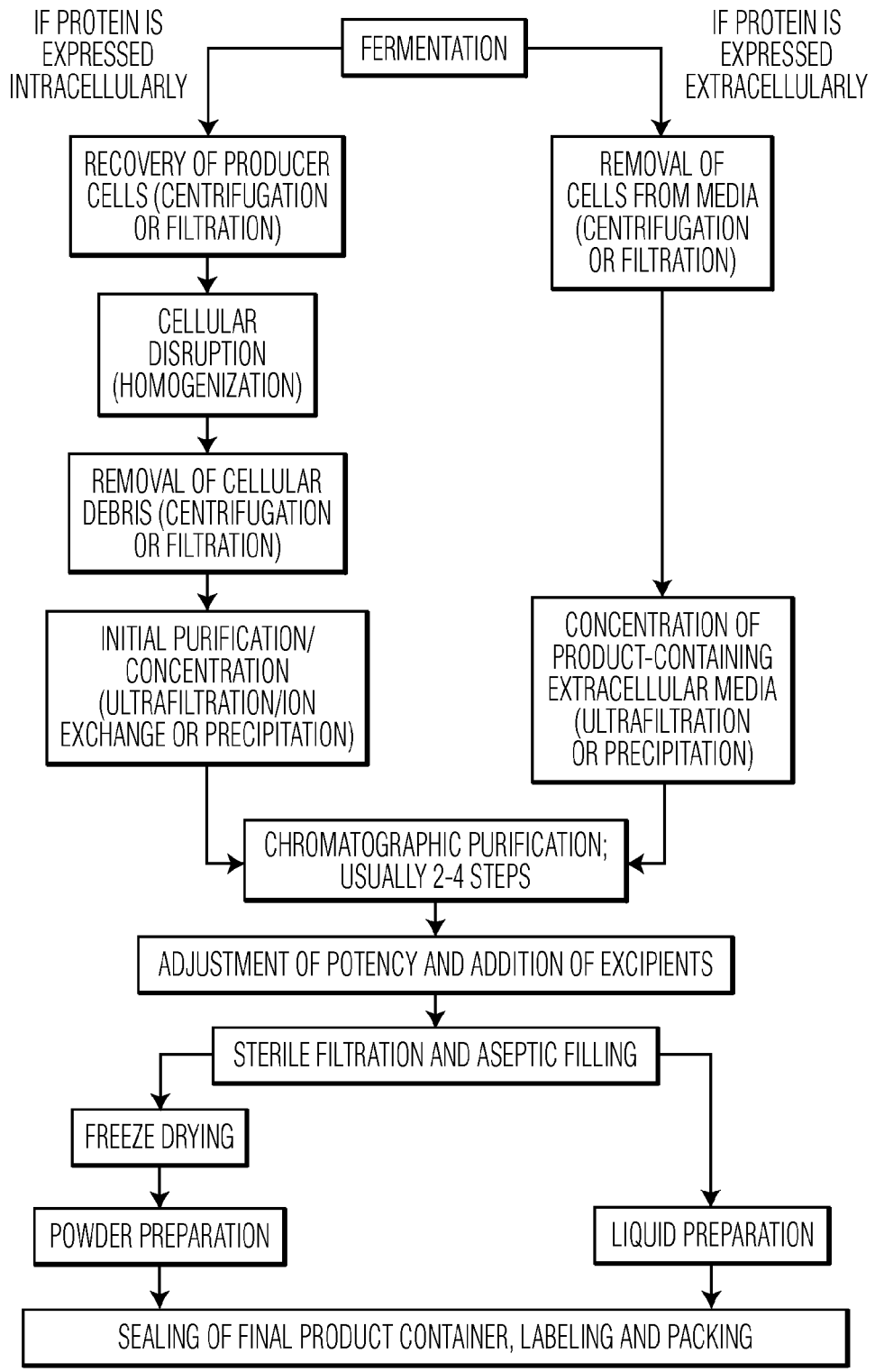
FIG. 1 shows a typical flow sheet for the manufacturing of protein biologics, both for proteins that are expressed intracellularly and proteins expressed extracellularly.
Figure 2:
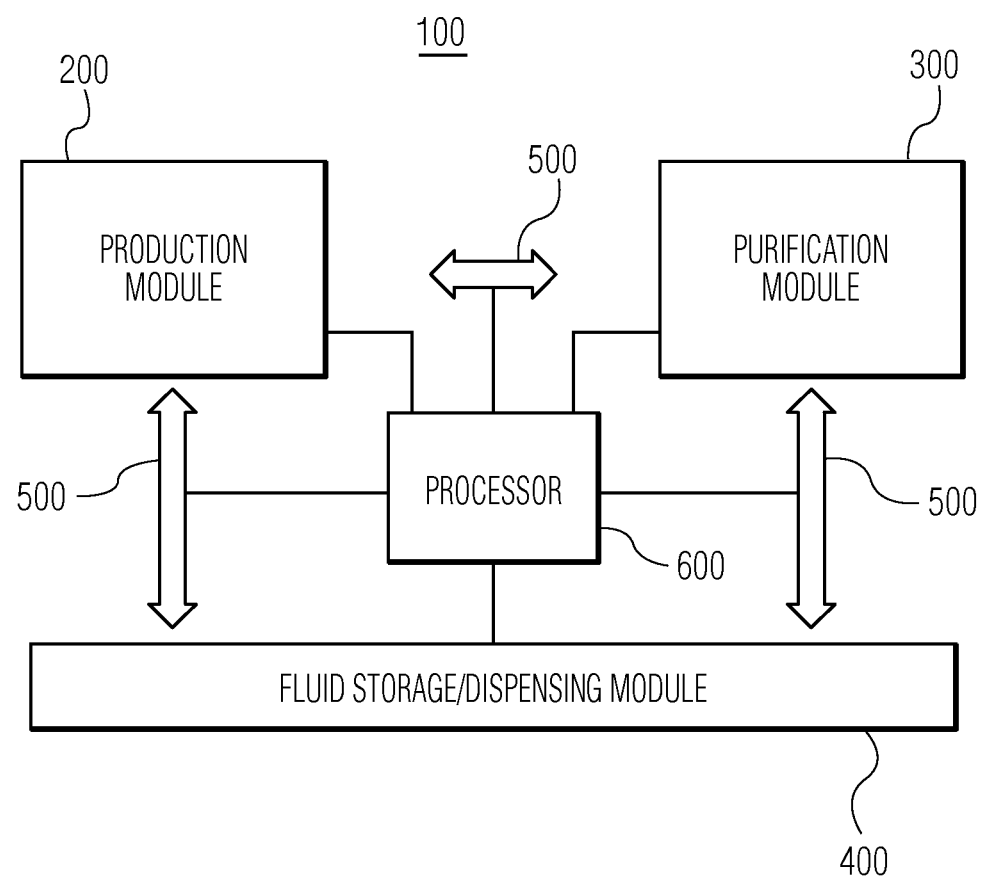
FIG. 2 is a block diagram that illustrates the principles of operation of one preferred embodiment of the present invention.

FIG. 2 is a block diagram that illustrates the principles of operation of one preferred embodiment of the present invention. The bioprocessing system 100 includes a production module 200, a purification module 300 and a fluid storage/dispensing module 400 that are fluidly coupled via coupling components 500. A processor 600 may be in electrical communication with one or more of the production module 200, purification module 300, coupling components 500 and fluid storage/dispensing module 400 for controlling and monitoring the operation of the system 100.

The fluid storage/dispensing module 400 is adapted to store the solutions needed for the production of a protein. The fluid storage/dispensing module 400 may also include containers for storing any waste product produced during the production of the protein. The fluid storage/dispensing module 400 may be temperature controlled, if needed, to maintain the solutions at a required temperature.

The production module 200 is adapted to receive the solutions required for production of a protein, such as a therapeutic protein, from the fluid storage/dispensing chamber via coupling components 500. The production module 200 may suitably include a bioreactor adapted for maintaining living cells that incorporates non-invasive optical chemical sensing technology for monitoring culture parameters (e.g., pH, oxygen, optical density, fluorescence, absorbance, redox, temperature, etc.), such as the bioreactors and optical chemical sensing technology illustrated and described in commonly assigned and related U.S. Pat. Nos. 6,673,532 and 7,041,493, as well as co-pending commonly assigned and related patent application Ser. No. 12/991,947, whose disclosures are incorporated by reference herein in their entirety. These types of bioreactors are particularly suited for cell-based production of therapeutic proteins. Alternatively, the production module 200 may suitably include a stirred mini-reactor such as, for example, the BIOGENIE® Minibioreactor sold by Scientific Bioprocessing, Inc., that is adapted for the cell-free production of a protein, and that are also equipped with sensors for monitoring reaction parameters (e.g., pH, oxygen, optical density, fluorescence, absorbance, redox, temperature, etc.)

After the reaction is complete, the raw product is then transferred to the purification module 300 via coupling components 500. The purification module 300 contains the necessary purification components for purifying the protein from the reagents. The purification module 300 can include, for example, chromatography components and dialyses components for purifying the biologic.

The production module 200 and the purification module 300 may each include sensors for monitoring reaction parameters and/or product quality parameters. The parameters monitored can include, but are no limited to, conductivity, temperature, pH, oxygen and $CO_2$. The sensors may be any type of invasive sensor known in the art for monitoring these parameters, where the sensors are in contact with the process fluid. In addition, the sensors may be non-invasive optical chemical sensors, such as those described in U.S. Pat. Nos. 6,673,532 and 7,041,493, and U.S. patent application Ser. No. 12/991,947. In addition, spectrometers known in the art can be used in the production module 200 and/or the purification module 300 to monitor the product stream and/or the inputs to each module. The parameters measured by such spectrometers can include, but are not limited to, absorbance, fluorescence, Raman scattering, circular dichroism and infrared spectral characteristics.

Figure 3:
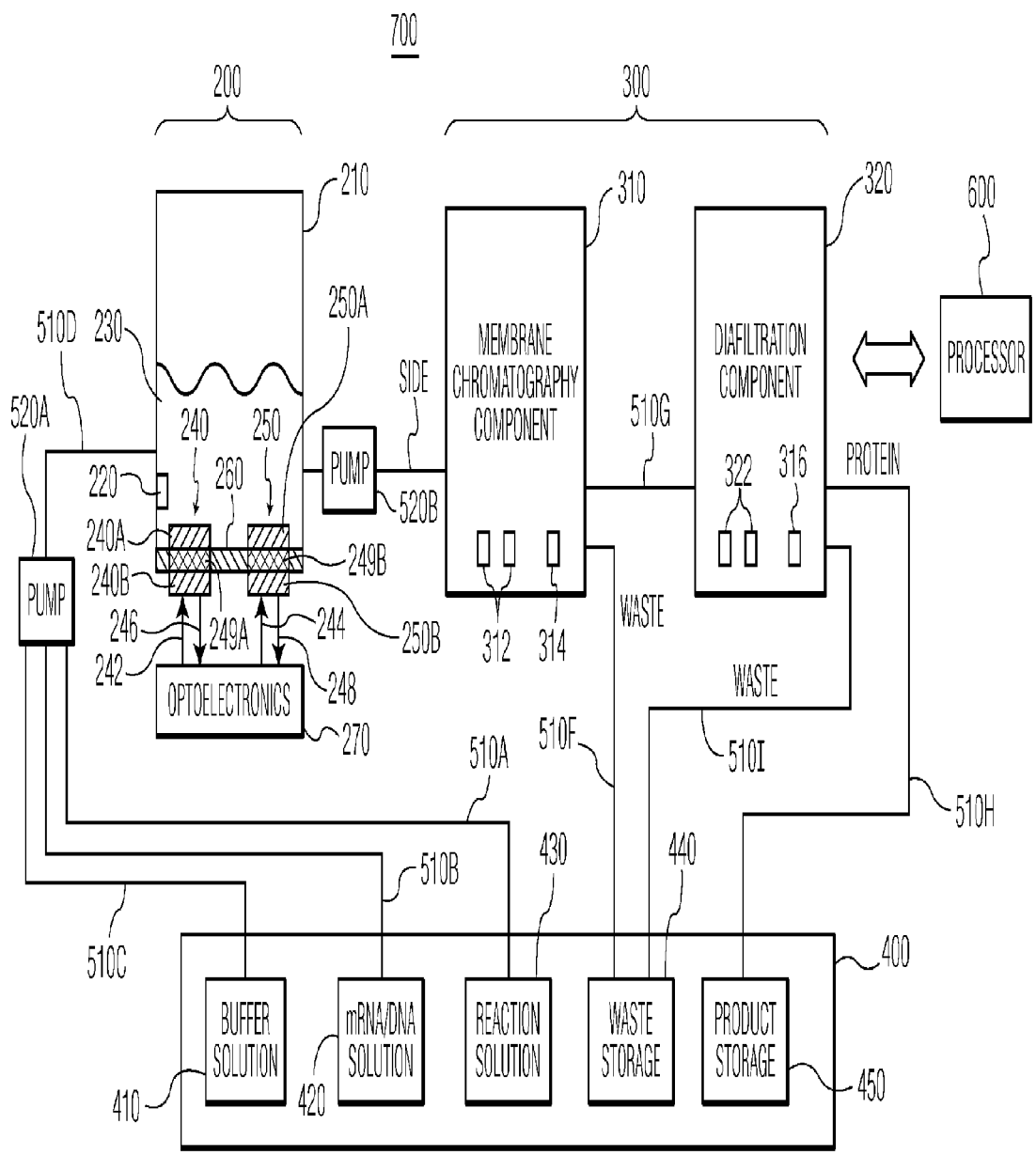
FIG. 3 is a schematic diagram of a bioprocessing system, in accordance with another preferred embodiment of the present invention.

FIG. 3 is a schematic diagram of a bioprocessing system 700, in accordance with another preferred embodiment of the present invention. The system 700 is particularly suited for the cell-free production of proteins and will be described in this context.

The system 700 includes a reactor 210, in which protein expression takes place, a membrane chromatography component 310, a diafiltration component 320 and a fluid storage/dispensing module 400. The reactor 210 preferably includes a heating and cooling element 220, suitably a thermoelectric cooler, for controlling the temperature of the solution 230 inside the reactor 210. The reactor also preferably includes sensors 240 and 250 for monitoring parameters in the reactor solution 230, such as pH, oxygen, redox, conductivity or any other parameter that can be measured with existing sensors. The sensors 240 and 250 can be implemented with any type of sensor known in the art for measuring the desired parameters. However, the sensors 240 and 250 are preferably non-invasive optical chemical sensors.

The system 700 also includes a processor 600 that is in communication with one or more of the reactor 210, optoelectronics 270, membrane chromatography component 310, diafiltration component 320, fluid storage/dispensing module 400 and pumps 520A and 520B for controlling and/or monitoring the operation of the system 700.

Optoelectronics 270 are provided for exciting the optical chemical sensors 240 and 250 with excitation light 242 and 244, respectively, and for receiving and detecting emission light 246 and 248 from the optical chemical sensors 240 and 250, respectively. As discussed above, commonly assigned and related U.S. Pat. Nos. 6,673,532 and 7,041,493, as well as co-pending commonly assigned and related U.S. patent application Ser. No. 12/991,947 describe in more detail how non-invasive optical chemical sensing technology can be used to monitor parameters.

In FIG. 3, two optical chemical sensors 240 and 250 are shown, and are preferably adapted to measure pH and dissolved oxygen, respectively. However any number of optical chemical sensors (including only one) may be used depending on the number and type of parameters being measured. Optoelectronics 270 include optical excitation sources (not shown) for generating the excitation light 242 and 244, as well as photodetectors (not shown) for detecting the emission light 246 and 248 from the optical chemical sensors 240 and 250. The type of optical excitation source or sources used in optoelectronics 270 are matched to the types of optical chemical sensors 240 and 250 used in the reactor 210. Any combination of optical excitation sources and optical chemical sensors may be used, depending on the number and types of parameters being measured. Examples of optical excitation sources that can be used included in optoelectronics 270 include, but are not limited to, light emitting diodes and laser diodes. Alternatively, the optoelectronics 270 may just be used to measure optical properties of the reactor contents in their entirety absent any sensors.

Further, for each optical chemical sensor 240 and 250, two possible placements on the reactor 210 are shown. The two possible placements for optical chemical sensor 240 are shown as 240A and 240B. The two possible placements for optical chemical sensor 250 are shown as 250A and 250B.

In the "A" placement (240A and 250A), the optical chemical sensors 240A and 250A are positioned inside the reactor 210 on a reactor wall 260. With this placement, the optical chemical sensors 240A and 250A are in physical contact with the solution 230, and the reactor wall 260 on which the optical chemical sensors 240A and 250A are placed is optically transparent to the excitation light 242 and 244, so that the excitation light can reach the optical chemical sensors 240A and 250A.

In the "B" placement (240B and 250B), the optical chemical sensors 240B and 250B are positioned outside the reactor 210 on reactor wall 260. With this placement, the thickness of the reactor wall 260 is sufficiently small so as to allow the analytes that are being measured to diffuse through the reactor wall 260 and contact the optical chemical sensors 240B and 250B. Alternatively, the portions of the reactor wall 260 on which the optical chemical sensors 240B and 250B are attached can replaced with barrier membranes 249A and 249B that are adapted to allow the analytes being measured to diffuse therethrough so that they come in contact with optical chemical sensors 240B and 250B. The use of barrier membranes and thin reactor walls to effectuate diffusion of the analytes of interest through a container wall to optical chemical sensors is described in more detail in commonly assigned and related U.S. patent application Ser. No. 13/378,033, which is incorporated herein by reference in its entirety.

In the FIG. 3 embodiment, the fluid storage/dispensing module 400 preferably includes a buffer solution container 410 for holding buffer solution, an mRNA/DNA solution container 420 for holding mRNA/DNA solution, a reaction solution container 430 for holding reaction solution, a waste storage container 440 for holding waste solution and a product storage container 450 for holding the purified protein. In operation, reaction solution, mRNA/DNA solution and buffer solution are directed to reactor 210 via conduits 510A, 510B, 510C and pump 520A.

After the reaction in the reactor 210, the raw product is directed to membrane chromatography component 310 via conduit 510E and pump 520B for purification of the protein from the reagents. Membrane chromatography component 310 may suitably include a cylindrically shaped housing which contains porous membrane layers (preferably at least 10 porous membrane layers), where the individual membranes consist of an appropriate polymer, such as polymethacrylate, that has been chemically functionalized with a ligand, such as a diethylaminoethyl (DEAE), a quaternary amine (Q), or a carboxymethyl (CM) ligand for the case of ion-exchange chromatography, or a phenyl or butyl ligand for the case of hydrophobic interaction chromatography, or a mercaptoethylpyridine (MEP) ligand for the case of mixed mode chromatography. One preferred embodiment of the membrane chromatography component 310 will be discussed in more detail below in connection with FIG. 5. Waste from the membrane chromatography process is directed to waste storage container 440 via conduit 510F. The purified product is directed to diafiltration component 320 for dialysis via conduit 510G and pump 520C.

Membrane chromatography component 310 may also include one or more sensors 312 for monitoring product quality parameters, such as conductivity, temperature, pH, oxygen, $CO_2$, absorbance, fluorescence, Raman, circular dichroism and infrared spectral characteristics. The sensors 312 may be any type of invasive or noninvasive sensor known in the art for measuring these parameters including, but not limited to, spectrometers. In addition, the sensors may be non-invasive optical chemical sensors, such as those described in U.S. Pat. Nos. 6,673,532 and 7,041,493, and U.S. patent application Ser. No. 12/991,947. In addition, membrane chromatography component 310 preferably includes a heating and cooling element 314, suitably a thermoelectric cooler, for controlling the temperature of the solution (raw product) inside the membrane chromatography component 310.

The diafiltration component 320 may suitably include a hydrophilic polymeric membrane, such as a polyethersulfone, a cellulosic, or a polyvinylidene fluoride (PVDF) membrane with a well defined pore structure that yields a desired molecular weight cut-off (MWCO) value in the range of 10 k to 200 k Da as appropriate for a given application. The final protein that comes out of the diafiltration component 320 is directed to product storage container 450 via conduit 510H. The waste product produced from the dialysis process in the diafiltration component 320 is directed to waste storage container 440 via conduit 510I.

Diafiltration component 320 may also include one or more sensors 322 for monitoring product quality parameters, such as conductivity, temperature, pH, oxygen, $CO_2$, absorbance, fluorescence, Raman, circular dichroism and infrared spectral characteristics. The sensors 322 may be any type of invasive or noninvasive sensor known in the art for measuring these parameters including, but not limited to, spectrometers. In addition, the sensors may be non-invasive optical chemical sensors, such as those described in U.S. Pat. Nos. 6,673,532 and 7,041,493, and U.S. patent application Ser. No. 12/991,947.

In addition, diafiltration component 320 preferably includes a heating and cooling element 316, suitably a thermoelectric cooler, for controlling the temperature of the solution (raw product) inside the membrane chromatography component 320.

In addition to the pumps 520A, 520B and 520C, any number of valves or other hydraulic components, such as additional pumps, may be used throughout the system 700 to assist in controlling the flow of solution/product between the various components of the system 700.

Figure 4:
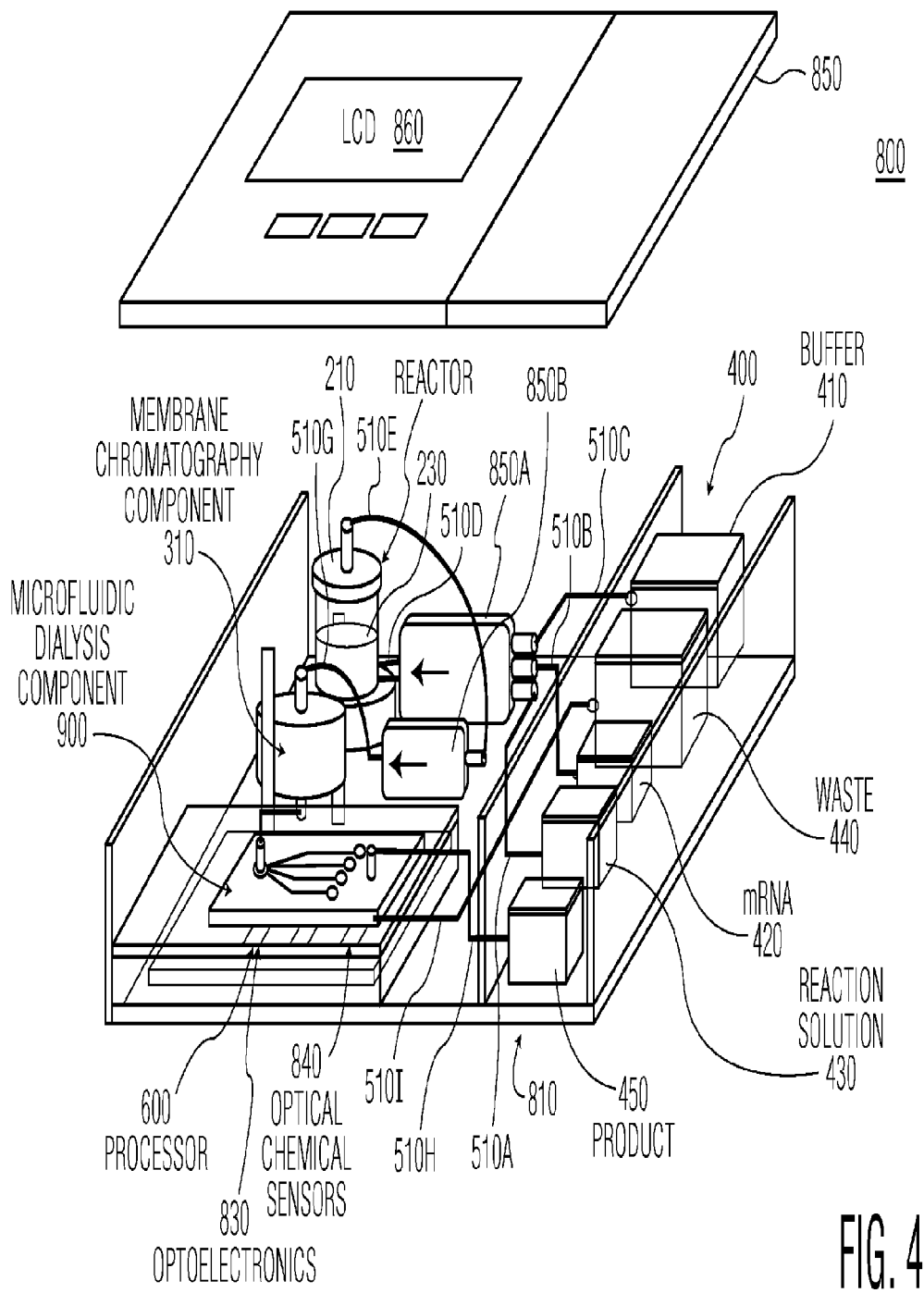
FIG. 4 is a schematic diagram of a microscale bioprocessing system, in accordance with another embodiment of the present invention.

The present invention is particularly suited to miniaturization by using micropumps and microfluidic technology. FIG. 4 is a schematic diagram of a microscale bioprocessing system 800, in accordance with another embodiment of the present invention. The system 800 includes many of the same components of the system 700 of FIG. 3, and common elements are labeled with common element numbers.

The system 800 contains a fluid storage/dispensing module 400 that includes a buffer solution container 410 for holding buffer solution, an mRNA/DNA solution container 420 for holding mRNA/DNA solution, a reaction solution container 430 for holding reaction solution, a waste storage container 440 for holding waste solution and a product storage container 450 for holding the purified protein. The system 800 also includes a reactor 210, a membrane chromatography component 310, a diafiltration component 820, a processor 600, optical chemical sensors 840 chosen and positioned to monitor finished product quality parameters, such as, for example, conductivity, redox, pH, UV spectrum and protein concentration, and optoelectronics 830 for providing optical excitation light and for detecting emission light from the optical chemical sensors 840. The optoelectronics 830 may also just be used to measure the optical properties of the finished product absent any sensors.

The reactor 210 can be of any size, but in the microscale embodiment of FIG. 4, it preferably has a volume capacity of less than approximately 50 milliliters, and more preferably approximately 20 milliliters or less, in order to keep the system 800 relatively compact. The reactor 210 may be implemented, for example, with the BIOGENIE® minibioreactor system manufactured by Scientific Bioprocessing, Inc.

Micropumps 850A and 850B and conduits 510A-510I direct solution to the various components in a manner similar to pumps 520A, 520B and conduits 510A-510I in the system 700 of FIG. 3. Although not shown in FIG. 4, the reactor 210 contains optical chemical sensors and optoelectronics for monitoring parameters in the reactor solution 230 in a manner similar to system 700 of FIG. 3. The micropumps 850A and 850B may be implemented with any type of micropump known in the art such as, for example, the mp5 micropump or the mp6 micropump manufactured by Bartels Mikrotechnik.

The housing lid 850 may contain a display, such as an LCD display 860, that connects to the processor 600 and that can provide information about the system 800, such as, for example, diagnostic information, reaction parameters and/or finished product quality parameters, such as, for example, conductivity, redox, pH, UV spectrum and protein concentration.

The processor 600 in FIGS. 2, 3 and 4 may be implemented with a general purpose desktop computer or a general purpose laptop computer. In addition, the processor may be implemented with a tablet computer or smartphone, such as iOS or Android-based tablets and smartphones. However, processor 600 can also be implemented with a special purpose computer, programmed microprocessor or microcontroller and peripheral integrated circuit elements, ASICs or other integrated circuits, hardwired electronic or logic circuits such as discrete element circuits, programmable logic devices such as FPGA, PLD, PLA or PAL or the like. In general, any device on which a finite state machine capable of executing code for implementing the functionality described herein can be used to implement the processor 600.

Figure 5:
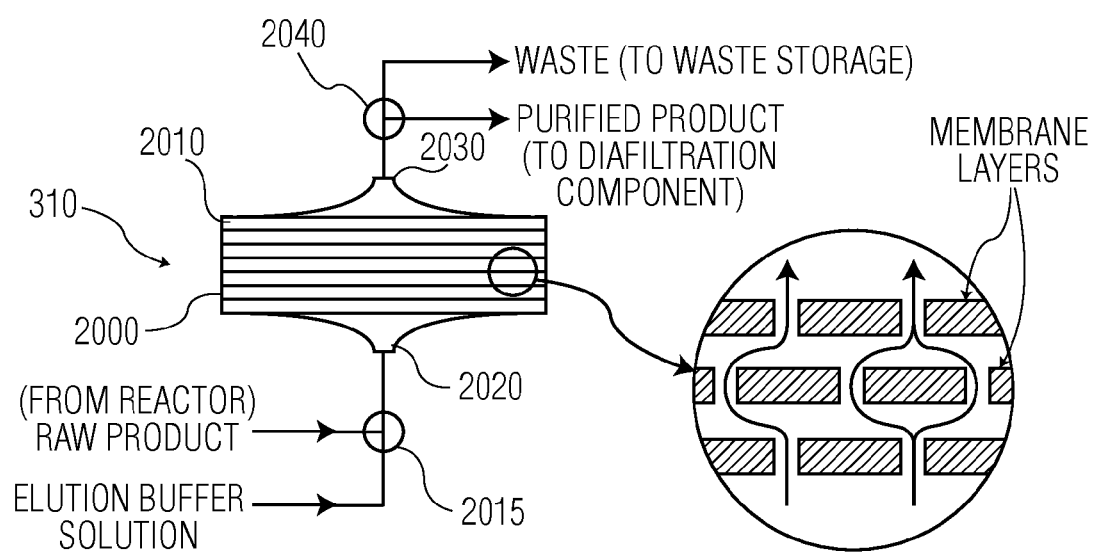
FIG. 5 is a side schematic view of a membrane chromatography component that can be used in the systems of FIGS. 3 and 4, in accordance with the present invention.

FIG. 5 shows a membrane chromatography component 310 that can be used in systems 700 and 800, in accordance with one preferred embodiment of the present invention. The membrane chromatography component 310 includes a housing 2000 and porous membrane layers 2010 (preferably at least 10 porous membrane layers). As discussed above, the individual porous membrane layers 2010 preferably consist of an appropriate polymer, such as polymethacrylate, that has been chemically functionalized with a ligand, such as a diethylaminoethyl (DEAE), a quaternary amine (Q), or a carboxymethyl (CM) ligand for the case of ion-exchange chromatography, or a phenyl or butyl ligand for the case of hydrophobic interaction chromatography, or a mercaptoethylpyridine (MEP) ligand for the case of mixed mode chromatography.

The membrane chromatography component 310 can be of any size, but in the microscale embodiment of FIG. 4, it preferably has a volume capacity of less than approximately 100 milliliters, and more preferably less than approximately 5 milliliters, in order to keep the system 800 relatively compact. The membrane chromatography component 310 may be implemented, for example, with a SARTOBIND® Q SingelSep Nano manufactured by Sartorius Stedim Biotech, which has a bed volume of 1 ml and a membrane area of 36 $cm^2$.

Raw product from reactor 210 is mixed with elution buffer solution via three-way valve 2015, and the mixture enters the membrane chromatography component 310 via inlet 2020. Purified product and waste exits via the outlet 2030. Three-way valve 2040 directs the purified product to the diafiltration component 320/900/1100 and directs the waste to waste storage 440.

Figure 6A:
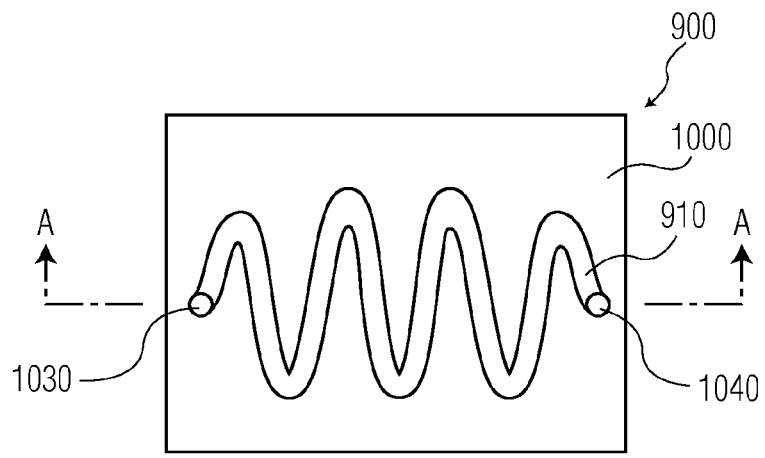
FIG. 6A is a top plan view of a microfluidic diafiltration component that can be used in the systems of FIGS. 3 and 4, in accordance with the present invention.
Figure 6B:
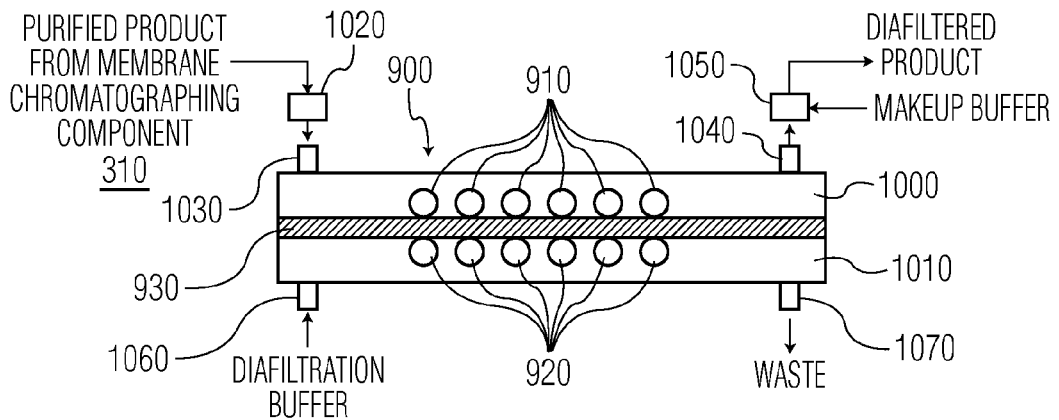
FIG. 6B is a schematic cross-sectional view of the equilibrium chamber of FIG. 6A looking along the cross-section line A-A of FIG. 6A.
Figure 6C:
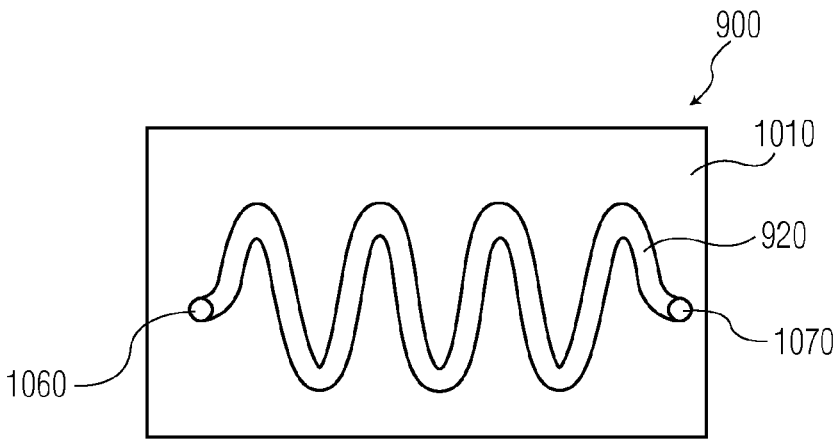
FIG. 6C is a bottom plan view of the equilibrium chamber of FIG. 6A.

FIGS. 6A-6C show a diafiltration component 900 that can be used in systems 700 and 800, in accordance with one preferred embodiment of the present invention. The diafiltration component 900 includes serpentine-shaped product and buffer sections 910 and 920, respectively. The diafiltration component 900 of FIGS. 6A-6C include a product section 910 that is a serpentine-shaped channel formed on a first substrate 1000. Similarly, the buffer section 920 is a channel formed on a second substrate 1010 with the same serpentine shape as the product section 910. A diafiltration membrane 930 is sandwiched between the first and second substrates 1000 and 1010, such that the serpentine-shaped channels that form the product and buffer sections 910 and 910 substantially overlap each other. The substrates 1000 and 1010 are attached to each other, with the diafiltration membrane 930 sandwiched between them, with any adhesive known in the art.

In the diafiltration component 900 of FIGS. 6A-6C, a diafiltration buffer solution flows through the serpentine-shaped product section 920 and purified product from the membrane chromatography component 310 flows through the serpentine-shaped product section 910. Diffusion takes place from the product section 910 to the counterpart, similarly shaped buffer section 920 via the diafiltration membrane 930.

The purified product from the membrane chromatography component 310 enters the product section 910 via inlet buffer reservoir 1020 and inlet 1030. The diafiltered product exits the product section 910 via outlet 1040 and outlet buffer reservoir 1050. Diafiltration buffer enters the buffer section 920 via inlet 1060 and exits the buffer section via outlet 1070. The diafiltration buffer is chosen to facilitate the transfer of components through the diafiltration membrane 930, and could be, for example, 25 millimolar phosphoric acid titrated to pH 7 with sodium hydroxide, or 25 millimolar citric acid tritrated to pH 5 with sodium hydroxide.

The inlet and outlet buffer reservoirs 1020 and 1050 are optionally used in order to dampen the back-and-forth oscillating flow, if needed. A makeup buffer solution is preferably added to the diafiltered product via the outlet buffer reservoir 1050 in order to replace the fluid that was that passed through the diafiltration membrane 930 with an equivalent volume of a different type of buffer, thereby transferring the protein of interest to the makeup buffer. Alternatively, the volume of the makeup buffer added via the outlet buffer reservoir 1050 can be less than the volume of fluid that has passed through the diafiltration membrane 930, in which case the diafiltration component 900 accomplishes both buffer exchange and protein concentration.

As discussed above, diafiltration membrane 930 may suitably be a hydrophilic polymeric membrane, such as a polyethersulfone, a cellulosic, or a polyvinylidene fluoride (PVDF) membrane with a well defined pore structure that yields a desired molecular weight cut-off (MWCO) value in the range of 10 k to 200 k Da as appropriate for a given application.

Figure 7:
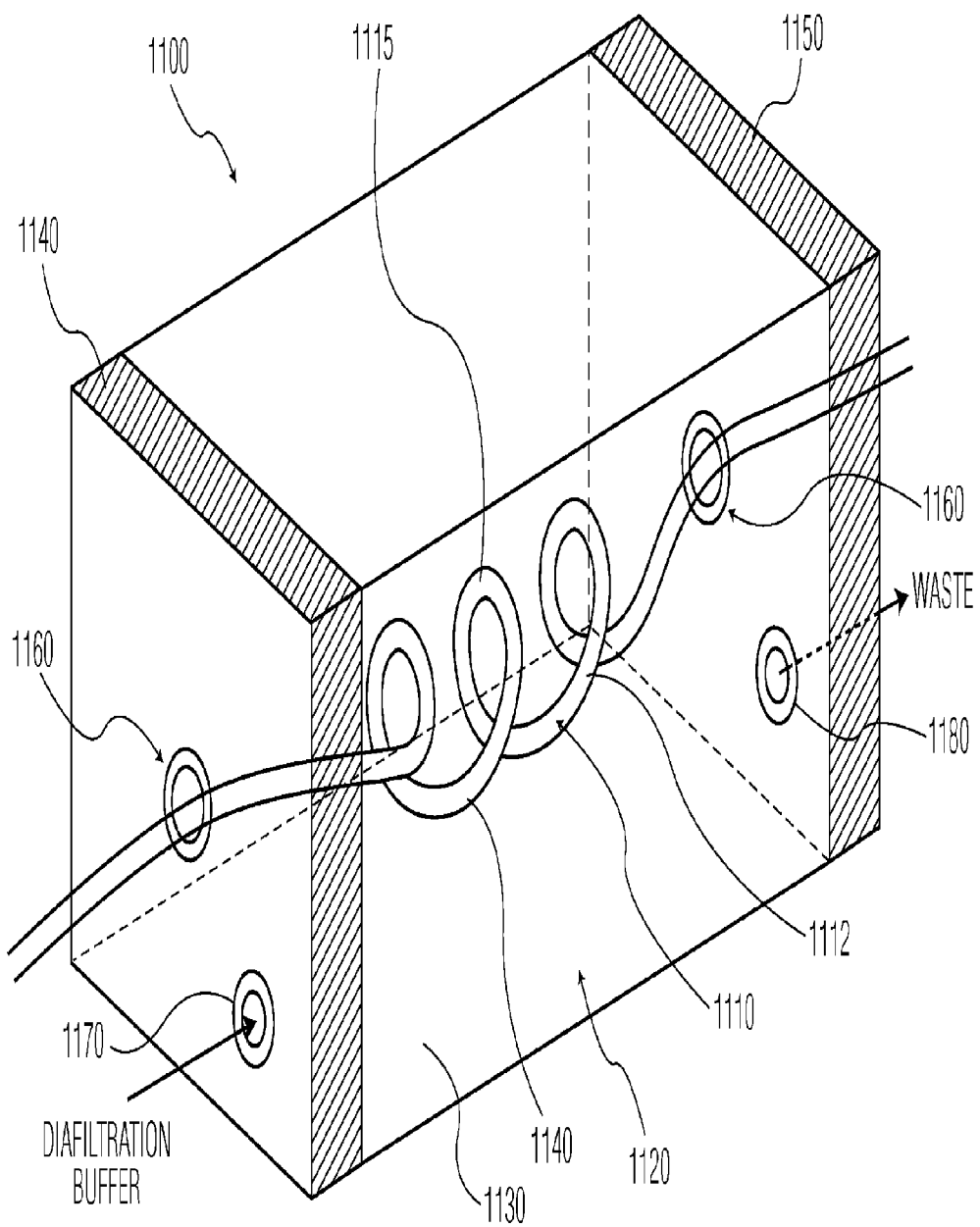
FIG. 7 is a perspective schematic view of another microfluidic diafiltration component that can be used in systems of FIGS. 3 and 4, in accordance with the present invention.

FIG. 7 shows a diafiltration component 1100 in accordance with another embodiment of the present invention. The diafiltration component 1100 may be used in system 700 or system 800 of FIGS. 3 and 4, respectively. The diafiltration component 1100 includes a buffer section 1120, and a product section 1110 that comprises tubing 1112 that is passed through the buffer section 1120. The tubing 1112 that makes up the product section 1110 can be any type of tubing known in the art that can function as the dialysis membrane 1140 between the product 1115 in the product section 1110 and the buffer 1130 in the buffer section 1120.

The tubing 1112 is preferably flexible so that a larger amount of tubing can be placed inside the solvent section 1120. The more tubing 1112 is present in the buffer section 1120, the more diffusion can take place between the tubing 1112 and the buffer 1130 due to the larger tubing surface area in contact with the buffer 1130. End portions 1140 and 1150 of the diafiltration component 1100 contain openings 1160 for the tubing 1112 to enter and exit the diafiltration component 1100. The end portions 1140 and 1150 also contain an inlet 1170 for receiving diafiltration buffer solution, and an outlet 1180 for expelling used diafiltration buffer solution (waste). Although the diafiltration component 1100 is shown as rectangularly-shaped, it can be any other shape, such as cylindrically-shaped. Further, the diafiltration component 1100 can suitably be a flow cell that has been modified to pass the tubing 1112 through the buffer section 1120.

Cell-Free Expression of Glucose Binding Protein

The systems and methods of the present invention can be used, for example, for the cell-free expression and purification of glucose binding protein (GBP). Glucose is a major carbon and energy source in cellular metabolism of animal body and in bioprocess industry. Glucose is not always beneficial in bioprocesses, it could also be detrimental in bacterial culture leading to self lysis of cells by formation of acetate in Krebs cycle and reducing the pH of the culture. Thus, fast and efficient concentration detection of glucose is is desired.

Glucose binding protein is a protein which could bind to glucose and serve this purpose by acting as a biosensor. GBP is a monomeric periplasmic protein with molecular weight of 34 kD (kilo Dalton) and is synthesized in the cytoplasm of E. coli. GBP binds to glucose with high affinity and could be used as a glucose biosensor. In vivo expression of GBP, which is also a conventional method of protein production, is cumbersome, expensive and time consuming. The present invention can provide a cell free expression and purification system at a small scale which could generate milligrams of quantity in few hours.

A biosensor is an analytical device used for the detection of an analyte that combines a biological component with a physicochemical detector component. GBP is such a biosensor, where GBP binds with glucose and binding is analyzed using fluorescence intensity and the corresponding signal is compared with standard glucose signal to estimate concentration of unknown sample. Using conventional in vivo methods, GBP is expressed in E. coli (L255C), followed by osmotic shock, purified by DEAE Sephadex A-50 column and dialysis using 10 kD membrane. An alternative method is cell-free expression, wherein cellular machinery is used for the protein expression and relatively fewer number of downstream purification operations are required for rapidly producing the desired protein.

In recent years, numerous proteins (12 to 135 kD) were expressed in cell-free systems of E. coli and wheat germ with the expression level ranging from a few micrograms to a few milligrams per milliliter in continuous flow cell-free expression mode. A combination of batch and continuous exchange methods have produced protein up to 6 mg/ml in E. coli S30 extract at a small scale. For all these protein expressions, reactors operating in different modes were studied with a membrane as an integral part of the system, separating the reaction mixture and feed solution. Continuous flow reactors are advantageous in terms of higher purity of proteins, higher productivity, toxic protein expression, computerization and easy control of the reaction due to the absence of a cell wall barrier. On the other hand, these reactors also pose the challenges of higher complexity and reactor costs, as well as solubility management of protein product.

In another study, expression of a fusion protein consisting of murine GM-CSF (granulocyte macrophage colony stimulating factor) and a scFv antibody, in reactor systems such as thin film, bubble column and Eppendorf tube without membrane, were studied, producing protein up to >500 μg/ml protein with significant amount of precipitated protein (≈50%). Recently, rhGM-CF was expressed in a 100 L stirred tank reactor expressing protein upto 700 mg/L which was subsequently purified with DEAE resin, tangential flow filtration membrane (3 kD cut off) and Sephacryl S-100 size exclusion chromatography with 99% purity and 65% recovery. Cell-free expression has not only been successful in the expression of bacterial proteins, but also successfully produced glycoproteins like human choriogonadotropin (hCG) and envelope glycoprotein (gp120) of human immunodeficiency virus type-1 (HIV-1) in hybridoma cell extract (HF10B4).

For protein purification, people have relied on column chromatography traditionally, but in recent years membrane chromatography has emerged as an additional aid in this field, eliminating column chromatography at specific steps like capture and polishing of protein at final step with overall cost reduction up to 65%. Column chromatography is still useful for gradient purification of proteins, but membrane chromatography could also be studied by relying on the fact that step elution of protein and removal of the impurities could be done at different buffer conditions.

The chart below compares cell-free and in vivo protein expression systems.

| In vivo | Cell free |
| --- | --- |
| Biological cell required | No cell, but cellular machinery is required |
| Time consuming process | Time effective process |
| Toxic protein could not be expressed | Toxic protein could be expressed |
| Multiple steps in purification required | Relatively less number of steps required |
| Higher fraction of misfolded protein along with folded protein | No misfolded protein reported, but precipitated |
| Higher endotoxins challenge | Relatively less endotoxins challenge |
| Higher amount of impurities in crude protein causing challenges in capture step | Relatively pure, enhancing capture and increasing yield of the protein |
| Established scale up | Has significant potential to scale up |
| Protein expression upto g/l | Protein expression upto mg/l |

Biomolecules for Protein Expression

The following biomolecules are preferably used for protein expression. To carry out a protein expression reaction, energy components and amino acids are supplied externally:

A genetic template for the target protein (mRNA or DNA) expression.

T7 RNA polymerases for mRNA transcription.

9 Translation factors (initiation, elongation and termination).

20 aminoacyl-tRNA synthetases (ARSes) for esterification of a specific amino acid to form an aminoacyl-tRNA.

Methionyl-tRNA transformylase transfers hydroxymethyl-, formyl-groups.

Creatine kinase converts ATP to ADP.

Myokinase catalyzes the inter conversion of adenine nucleotides.

Pyrophosphatase are acid anhydride hydrolases that act upon diphosphate bonds.

4 nucleoside triphosphates (ATP,GTP,CTP,TTP) for DNA formation.

Creatine phosphate serves as a rapidly mobilizable reserve of high-energy phosphates.

10-formyl-5,6,7,8-tetrahydrofolate important in the formylation of the methionyl initiator tRNA (fMet-tRNA).

20 amino acids for protein synthesis.

Ribosomes for polypeptide translation.

46 tRNAs in protein synthesis.

Cellular components which assist in proper protein folding.

Mechanism of Protein Expression in In Vivo and Cell-Free Systems

Figure 8:
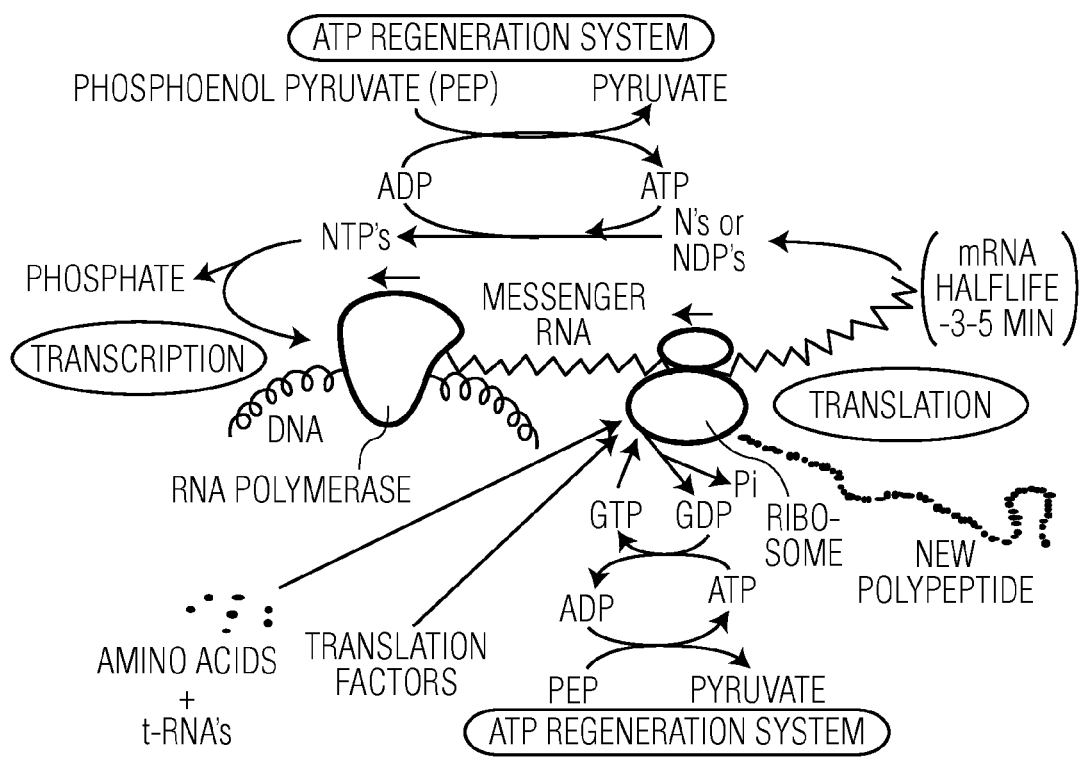
FIG. 8 is a diagram showing the main steps in in vivo protein expression.

Protein is expressed in three main steps involving replication, transcription and translation, as shown in FIG. 8. With regards to the replication step, the blueprints for proteins are stored in cell's DNA. DNA multiplies to make multiple copies by a process called replication. DNA polymerase is an enzyme that synthesizes new DNA by adding new nucleotides along with other proteins which are associated with the fork and assist and continuation of DNA synthesis.

Transcription occurs in three steps in both prokaryotes and eukaryotes: Initiation, Elongation and Termination. The initiation of transcription occurs when the double-stranded DNA is unwound to allow the binding of RNA polymerase. Once transcription is initiated, the RNA polymerase is released from the DNA. Transcription is regulated at various levels by activators and repressors, and also by chromatin structure in eukaryotes.

In prokaryotes, no special post-transcriptional modification of mRNA is required. However, in eukaryotes, mRNA is further processed to remove introns (splicing), to add a 'cap' (M7 methyl-guanosine) at the 5' end and to add multiple adenosine ribonucleotides at the 3' end of mRNA to generate a poly(A) tail. The modified mRNA is then translated.

The translation or protein synthesis is also a multi-step process with Initiation, Elongation and Termination steps and is similar in both prokaryotes and eukaryotes. The process requires cellular components such as ribosomes, transfer RNAs (tRNA), mRNA and protein factors as well as small molecules like amino acids, ATP, GTP and other cofactors.

Cell-Free Protein Expression from an Engineer's Perspective

Cell extract is prepared after cell lysis and removal of cell wall. Protein could be synthesized using DNA or mRNA template by adding into the cell extract. When DNA is used as template (i.e. linked reaction), it first transcribes to mRNA in the presence of translation mixture and protein is expressed. Alternatively mRNA could also be used for this purpose. Another way of protein expression is the coupled reaction where transcription and translation reactions are carried out in the same tube with all necessary components for both reactions. In either case, mRNA is ultimately translated in the cell extracts without the need for purification of the message.

Conventional and Non-Conventional Method of GBP Production

In the conventional method, GBP is produced in multiple steps like pre-inoculation of *E. coli* mutants (L225C) in Luria Bertani (LB) broth, culturing, harvesting, cell washing, osmotic shock, labeling, liquid chromatography and dialysis. All these steps are time consuming (around 4 days) and cumbersome. The present invention enables a non-conventional cell free expression of GBP where expression is faster and the resulting protein is relatively pure. This protein would preferably be labeled using a fluorophore called acrylodan (6-Acryloyl-2-dimethylaminonaphthalene) and purified by D15 (DEAE) chromatography membrane. The protein would preferably further be concentrated and dialyzed against 5 mM tris-HCl, pH 7.5.

The foregoing embodiments and advantages are merely exemplary, and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. Various changes may be made without departing from the spirit and scope of the invention, as defined in the following claims. For example, although the present analyte sensor system has been predominantly described in connection with a $CO_2$ sensing system, it can be applied to any fluorescence based sensing system. Further, although the present analyte sensor system has been described as being particularly suited for monitoring large bodies of water, such as oceans and lakes, they can be used to monitor analytes in any type of liquid or gas media, such as liquid or gas media inside a bioreactor.

What is claimed is:

1. A bioprocessing system, comprising:
   a reactor adapted for cell-free protein expression that produces a protein utilizing cell-free protein expression;
   at least one sensor for monitoring reaction parameters in the reactor; and
   a purification module for receiving the protein from the reactor and for purifying the protein from reagents, wherein the purification module comprises,
      a chromatography component for receiving the protein from the production module and for outputting purified protein, and
      a diafiltration component comprising a product section for receiving the purified protein from the chromatography component and a buffer section for receiving a buffer solution, wherein the diafiltration component outputs further purified protein, and wherein the diafiltration component further comprises,
         a first substrate,
         a second substrate, and
         a diafiltration membrane positioned between the first and second substrates.

2. The system of claim 1, further comprising:
   a first heating and cooling element positioned inside the reactor for controlling a temperature solution inside the reactor; and
   a second heating and cooling element positioned inside the diafiltration component for controlling a temperature of solution inside the diafiltration component.

3. The system of claim 1, wherein the at least one sensor comprises at least one optical chemical sensor positioned inside the reactor.

4. The system of claim 1, wherein the reactor has a capacity of approximately 20 ml or less.

5. The system of claim 1, wherein the chromatography component comprises a membrane chromatography component.

6. The system of claim 1, wherein the product section comprises a serpentine-shaped channel formed on the first substrate and the buffer section comprises a serpentine-shaped channel formed on the second substrate, wherein the first and second serpentine-shaped channels substantially overlap each other.

7. The system of claim 1, wherein the diafiltration component comprises a flow cell.

8. The system of claim 7, wherein the product section comprises tubing positioned within the flow cell and the diafiltration membrane comprises the tubing material.

9. The system of claim 1, wherein the at least one sensor monitors at least one of conductivity, temperature, pH, oxygen, redox and $CO_2$.

10. The system of claim 1, wherein the at least one sensor comprises an optical chemical sensor.

11. The system of claim 1, wherein the purification module comprises at least one sensor for monitoring product quality parameters.

12. The system of claim 11, wherein the at least one sensor is positioned inside the chromatography component.

13. The system of claim 11, wherein the at least one sensor monitors at least one of absorbance, fluorescence, Raman scattering, circular dichroism and infrared spectral characteristics.

14. The system of claim 13, wherein the at least one sensor is positioned inside the chromatography component.

15. The system of claim 1, wherein the at least one sensor comprises at least one optical chemical sensor positioned outside the reactor on a portion of the reactor wall, and wherein a thickness of the portion of the reactor wall on which the at least one optical chemical sensor is positioned is sufficiently small so as to allow analytes being measured to diffuse through the portion of the reactor wall.

16. The system of claim 1, further comprising a fluid storage and dispensing module for storing solutions used by the production module for protein expression and for storing waste product produced by the purification module.

17. The system of claim 16, wherein the fluid storage and dispensing module also stores purified protein output by the purification module.

18. The system of claim 1, further comprising a processor for controlling and/or monitoring at least one of the reactor and the purification module.

19. A method, comprising producing a protein on-demand using the system of claim 1.

* * * * *